(12) United States Patent
Budhwani et al.

(10) Patent No.: US 11,833,514 B2
(45) Date of Patent: *Dec. 5, 2023

(54) BIOMIMETIC ARRAY DEVICE AND METHODS OF USING SAME

(71) Applicant: CERFLUX, INC., Birmingham, AL (US)

(72) Inventors: Karim I. Budhwani, Birmingham, AL (US); Brahma Mubarak K. Budhwani, Birmingham, AL (US); Khidr Kishan K. Budhwani, Birmingham, AL (US)

(73) Assignee: Cerflux, Inc., Birmingham, AL (US)

( * ) Notice: Subject to any disclaimer, the term of this patent is extended or adjusted under 35 U.S.C. 154(b) by 80 days.

This patent is subject to a terminal disclaimer.

(21) Appl. No.: 17/385,683

(22) Filed: Jul. 26, 2021

(65) Prior Publication Data

US 2021/0346890 A1    Nov. 11, 2021

Related U.S. Application Data

(63) Continuation of application No. 16/684,287, filed on Nov. 14, 2019, now Pat. No. 11,097,274.

(Continued)

(51) Int. Cl.
   *B01L 3/00*      (2006.01)
   *G01N 33/50*     (2006.01)
   *G01N 33/483*    (2006.01)

(52) U.S. Cl.
   CPC ... *B01L 3/502761* (2013.01); *B01L 3/502707* (2013.01); *B01L 3/502746* (2013.01);
   (Continued)

(58) Field of Classification Search
   CPC ......... B01L 3/502761; B01L 3/502746; B01L 3/502707; B01L 2300/0829; B01L 2300/0877; G01N 33/4833; G01N 33/5008
   See application file for complete search history.

(56) References Cited

U.S. PATENT DOCUMENTS

2004/0149659 A1   8/2004  Kane
2005/0043894 A1   2/2005  Fernandez
(Continued)

FOREIGN PATENT DOCUMENTS

CN   101274469 A   10/2008
CN   104836620 A   8/2015
(Continued)

OTHER PUBLICATIONS

Dereli-Korkut, Zeynep et al., "Three dimensional microfludic cell arrays for ex vivo drug screening with mimicked vascular flow." Analytical Chemistry, Feb. 25, 2014. vol. 86, pp. 2997-3004 abstract; p. 2998; and Figs. 1,2.

(Continued)

*Primary Examiner* — Jennifer Wecker
*Assistant Examiner* — Kathryn Elizabeth Limbaugh
(74) *Attorney, Agent, or Firm* — C. Brandon Browning; Maynard Nexsen PC

(57) ABSTRACT

The present disclosure generally pertains to a biomimetic array device and methods of using the device to expose biological samples to an array of fluids. The device includes a cassette and an inlet region, where the cassette comprises at least one microchamber array and at least one microchannel. Each microchamber within a microchamber array has a top interface that is open to the external environment, so that a biological sample placed at the top interface is positioned to draw fluid from the microchambers. The inlet region (Continued)

comprises at least one well and at least one inlet channel, each well in fluid communication with one inlet channel. Fluid deposited into wells flows through each inlet channel and microchannel in fluid communication with each well containing fluid, so that each microchamber within one microchamber array provides an approximately equal volume of fluid to the biological sample.

18 Claims, 7 Drawing Sheets

Related U.S. Application Data

(60) Provisional application No. 62/782,523, filed on Dec. 20, 2018.

(52) U.S. Cl.
CPC ..... *G01N 33/4833* (2013.01); *G01N 33/5008* (2013.01); *B01L 2300/0829* (2013.01); *B01L 2300/0877* (2013.01)

(56) References Cited

U.S. PATENT DOCUMENTS

| | | |
|---|---|---|
| 2006/0234298 A1 | 10/2006 | Chiu et al. |
| 2012/0164679 A1* | 6/2012 | Vrouwe ............... C12M 23/16 435/287.1 |
| 2017/0095818 A1 | 4/2017 | Liu et al. |
| 2017/0259266 A1 | 9/2017 | Yamawaki et al. |
| 2018/0320125 A1 | 11/2018 | Levner et al. |

FOREIGN PATENT DOCUMENTS

| | | |
|---|---|---|
| JP | 2017158491 A | 9/2017 |
| KR | 10-2010-0060471 A | 6/2010 |

OTHER PUBLICATIONS

Wu, Min-Hsien et al., "Microfluidic cell culture systems for drug research." The Royal Society of Chemistry. 2010, vol. 10, pp. 939-956.
Hiroshi, Kimura et al., "Organ/body-on-a-chip based on microfluidic technology for drug discovery." Drug Metabolism and Pharmacokinetics, 2018, vol. 33, pp. 43-48.
Nannan Ye et al., "Cell-based high content screening using an integrated microfluidic device." 2007, RSC Publishing/Lab on a Chip, vol. 7, pp. 1696-1704.
Examiner Requisition for Canadian Patent Application No. 3124645, dated Jan. 25, 2023, pp. 4.
First Search Report for Chinese Patent Application No. 2019800926491, dated May 27, 2022, p. 1.
International Preliminary Report on Patentability for International Application No. PCT/US2019/067969, dated Jul. 1, 2021, pp. 5.
International Search Report and Written Opinion for International Application No. PCT/US2019/067969, dated Apr. 21, 2020, pp. 7.
Supplementary European Search Report and Written Opinion for European Application No. 19898519.4, dated Sep. 14, 2022, pp. 7.

* cited by examiner

BIOMIMETIC ARRAY DEVICE AND METHODS OF USING SAME

CROSS REFERENCE TO RELATED APPLICATION

This application claims priority to U.S. Non-provisional patent application Ser. No. 16/684,287, entitled, "Biomimetic Array Device and Methods of Using Same," filed on Nov. 14, 2019, which claims priority to U.S. Provisional Patent Application No. 62/782,523, entitled, "Simple Microchamber Array Technology (SMART) and Method of Use," filed on Dec. 20, 2018, and, which is incorporated herein by reference.

TECHNICAL FIELD

The present invention is directed to an array device and methods of using the device for the exposure of biological samples to arrays of fluids.

BACKGROUND OF INVENTION

Understanding the interactions between therapeutic agents and biological targets is important in the development and administration of effective therapeutic regimens. However, disease-associated cells and tissue vary not only between patients, but within an individual patient. Thus, a therapeutic regimen may be effective for some patients, but less effective or ineffective for others. Similarly, a therapeutic regimen that works for a patient may become less effective over the duration of treatment due to disease progression or other dynamic physiological phenomena. For example, conventional approaches to tumor treatment includes iteratively trying therapeutic regimens on a patient until an effective regimen is established. This approach is time-consuming and expensive, often delaying effective treatment and allowing disease progression in the interim. Additionally, treatment presents challenges to the patient, who may suffer unpleasant and taxing side-effects while undergoing ultimately ineffective therapies.

As alternative to in vivo treatment evaluation using a patient's body, animal models, cellular in vitro models, and organoids have been utilized to discern how potential therapeutics effect biological samples. However, cost and time burdens make these approaches difficult to apply when evaluating multiple potential therapy agents. Additionally, in some cases, these approaches may not accurately model the physiological conditions present in the patient's body and thus produce unclear or uncertain results. The present disclosure provides a device and method of evaluating an array of fluids, including therapeutic agents, to a biological sample in a time-efficient and low cost manner. The biological sample may include a tumor tissue slice culture from a patient, which has preserved microarchitecture and does not require the addition of growth factors, in contrast with other methods which typically involve dissociation and/or expansion of the original tissue. Thus, several treatment options may be evaluated simultaneously by applying the array of therapeutic agents to the biological sample and observing cell viability and characteristics of the biological sample in each region of therapeutic agent exposure.

SUMMARY OF THE INVENTION

The present invention is directed to a biomimetic array device and methods of using same. In one aspect of the invention, there is provided biomimetic array device including a cassette with at least one microchamber array and at least one microchannel or set of microchannels, where each microchamber array includes at least one microchamber in fluid communication with at least one microchannel. Each microchamber has a top interface that is open to its external environment and is configured to receive a biological sample along its top interface, so that the biological sample at the top interface is positioned to draw fluid from the microchamber when the microchamber contains fluid. The device further includes an inlet region with at least one well and at least one inlet channel, where each well is in fluid communication with an intake region of one inlet channel and the intake region of each inlet channel is in fluid communication with one well. The wells are each configured to receive fluid through a top opening and direct fluid into the intake region of one inlet channel though a port located in a base of the well. Each inlet channel has an intake region for receiving fluid from one well and a transport region for transporting fluid from the intake region to at least one microchannel in the cassette. The biomimetic array device is configured to transport approximately equal volumes of fluid from each well to each microchamber that is in fluid communication with each well, so that each microchamber within one microchamber array is configured to provide an approximately equal volume of fluid to the biological sample at the top interface of each microchamber.

In some embodiments, at least one inlet channel is branched into more than one inlet sub-channels within the transport region, and each inlet sub-channel is in fluid communication with at least one microchannel. The connection of at least two microchamber arrays may be in parallel or in series, and the device is of unitary construction and composed of a hydrophilic material. In some instances, a hydrophobic coating is placed on regions of the device to substantially prevent spilling of fluid from the device or unintended wetting of tops of adjacent walls. Microchannels have varying depths within the cassette and no adjacent microchannels have the same depth, so that fluid transport between adjacent microchannels is substantially prevented. Similarly, microchannels have varying lengths across the cassette and no adjacent microchannels have the same length, so that fluid transport between adjacent microchannels is substantially prevented. To prevent fluid from spilling from the device in instances where the device is agitated and to hold a biological sample, sidewalls of the cassette are higher along microchannels and lower along microchambers. To aid in mixing fluids, in some instances at least one microchannel and/or at least one inlet channel includes agitation structures that extend from its interior surface for mixing fluid components.

In some embodiments, at least one well contains a spacing structure within its interior that reduces a cross sectional area parallel to its base, so that said at least one well is configured to hold a volume of fluid at a greater height within its interior than would occur for the same volume of fluid without the spacing structure. Sizes of the spacing structures are determined by lengths of the inlet channels, with larger spacing structures in wells that are in fluid communication with longer inlet channels, so that the device is configured to transport equal volumes of fluid deposited into each well to each microchamber within one microchamber array and to provide equal exposure of fluid to the biological sample at the top interface of each microchamber.

In another aspect of the invention, there is provided a method of using a biomimetic array device. The method includes first providing a biomimetic array device, where the device includes a cassette and an inlet region. The cassette includes at least one microchamber array and at least one microchannel or set of microchannels, each microchamber array having at least one microchamber in fluid communication with at least one microchannel. Each microchamber has a top interface that is open to its external environment and configured to receive a biological sample along the top interface. The inlet region includes at least one well and at least one inlet channel, each well in fluid communication with one inlet channel and each inlet channel in fluid communication with one well. Each well is configured to receive fluid through a top opening and direct the fluid into one inlet channel though a port located in a base of the well, and each inlet channel is in fluid communication with at least one microchannel in the cassette. A second step includes positioning a biological sample along the top interface of at least one microchamber in each microchamber array. After the biological sample is positioned, an operator deposits fluid within at least one well, where the fluid flows through each inlet channel and microchannel in fluid communication with each well containing the deposited fluid, so that each microchamber within one microchamber array provides an approximately equal volume of fluid to the biological sample at the top interface of each microchamber. In some embodiments, biological sample is positioned after fluid fills the microchambers. In some embodiments, biological samples are subjected to sequential filling and emptying of microchambers with the same or different fluids to simulate various therapeutic cycles or to monitor disease progression post treatment or for the evaluation of preclinical therapeutic formulations during therapeutic discovery. In some embodiments, additional hydrogel matrix is integrated with the biological sample. In some embodiments, the hydrogel matrix is infused with patterned nano particles for electromagnetic impulse analysis. In some additional embodiments, the hydrogel matrix is infused with other whole or dissociated connective tissue or liquid biopsy specimen from the same patient, cell lines, animal models, or otherwise established source.

An equal volume of fluid is deposited in each well, and the fluid deposited in any well of the at least one well is selected from the group consisting of culture media, a therapeutic agent, or a pharmaceutical compound. The biological sample includes tumor tissue from a patient or tissue integrated with additional components, including hydrogel matrix, as described above. The method may further include the step of characterizing the phenotype, response, and viability of cells within the tumor tissue after exposure to fluid, so that fluids that result in the target cell death mode and magnitude are identified as therapeutic candidates for the patient.

In yet another aspect of the invention, there is provided a biomimetic array device. The device includes a cassette with at least one microchamber array and at least one microchannel or set of microchannels, each microchamber array having at least one microchamber in fluid communication with at least one microchannel. Each microchamber and each microchannel include a top interface that is open to its external environment. Microchannels have alternating depths and alternating lengths with longer microchannels being shallower and shorter microchannels being deeper, so that microchannels are configured to hold equal volumes of fluid and so that fluid transport between adjacent microchannels is substantially prevented. The device further includes an inlet region with at least one well and at least one inlet channel, each well configured to receive fluid through a top opening and direct the fluid into one inlet channel though a port located in a base of the well, with each inlet channel configured to transport fluid to at least one microchannel in the cassette. The biomimetic array device is configured to transport approximately equal volumes of fluid from each well to each microchamber that is in fluid communication with each well, so that each microchamber within one microchamber array is configured to provide an approximately equal volume of fluid to a biological sample positioned at the top interface of each microchamber.

In some embodiments, wells are of approximately the same shape and size and are positioned in at least one row of wells, the wells within each row having approximately even spacing. In some embodiments, at least one well contains a spacing structure within its interior that reduces a cross sectional area parallel to its base, so that said at least one well is configured to hold a volume of fluid at a greater height within its interior than would occur for the same volume of fluid without the spacing structure. Sizes of the spacing structures are determined by lengths of the inlet channels, with larger spacing structures in wells that are in fluid communication with longer inlet channels, so that the device is configured to transport equal volumes of fluid deposited into each well to each microchamber within one microchamber array and to provide equal exposure of fluid to the biological sample positioned at the top interface of each microchamber.

A further understanding of the nature and advantages of the present invention will be realized by reference to the remaining portions of the specification and the drawings.

BRIEF DESCRIPTION OF DRAWINGS

The present disclosure same can be better understood, by way of example only, with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION OF THE INVENTION

Figure 1:
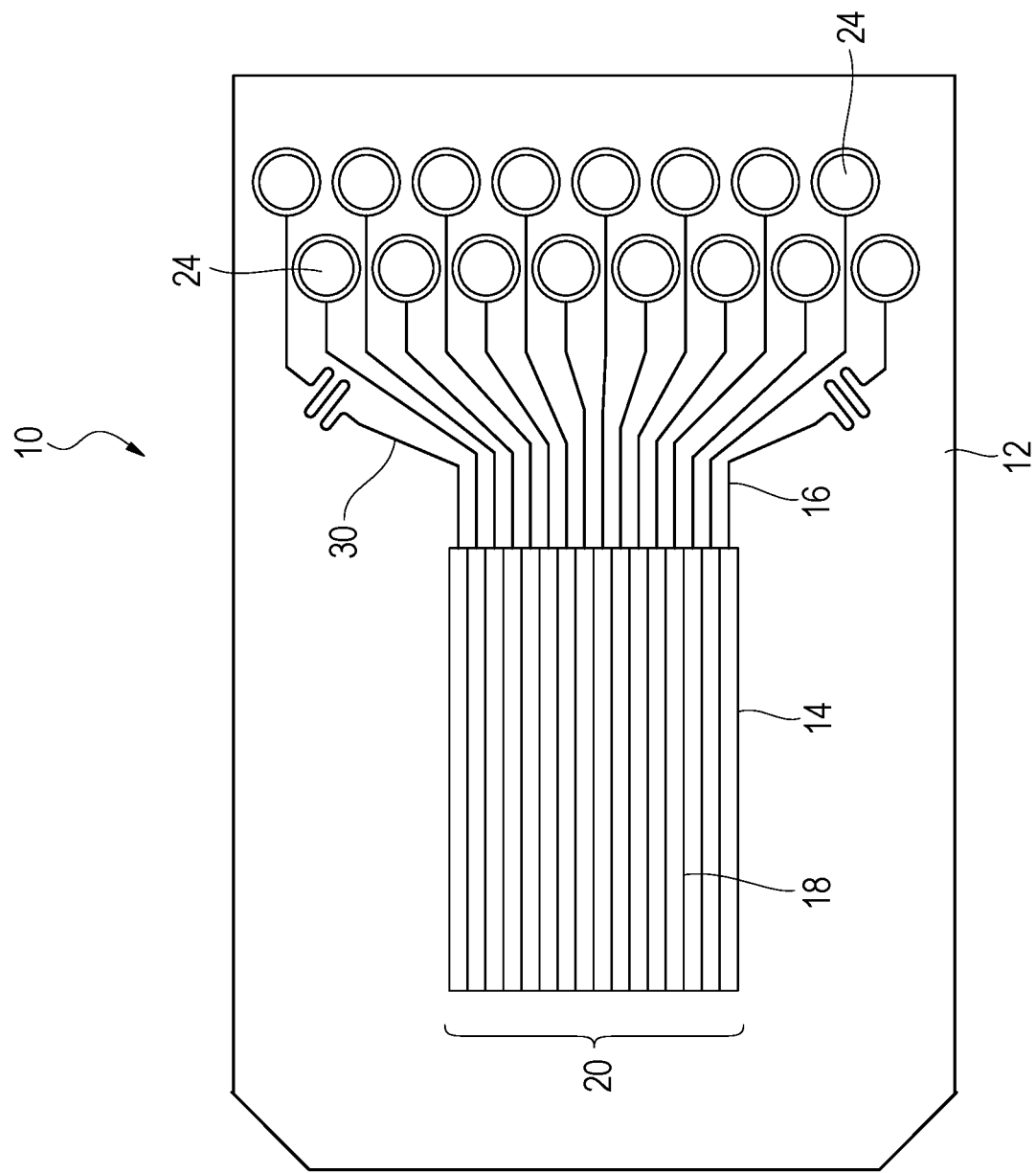
FIG. 1 is a top view of a schematic depicting a biomimetic array device with microchannels that are configured to transport fluid through microchannels to microchambers.

The present invention is generally directed to a biomimetic array device 10 and methods of using same. Biomimetic array device has an inlet region 12 for receiving fluid and a cassette 14 for transporting fluid through microchannels 16 to microchambers 18 within a microchamber array 20. A biological sample 22, when placed above a microchamber array 20, is thus exposed to various fluids present in the microchambers 18 that make up the microchamber array 20. When biological sample 22 is a tumor tissue sample from a patient, the result of exposure to various fluids is assessed by observing cell viability within exposed regions of the tumor tissue sample. In these instances, fluids may be therapeutic drug candidates. Thus, multiple therapeutic treatments for an individual patient may be assessed simultaneously in a biomimetic, in vitro setting, as opposed to conventional in vivo therapeutic regimen assessments, where treatments are conducted on the patient iteratively until an appropriate regimen is identified.

As used herein, the singular forms "a," "an," and "the" include plural referents unless the context clearly indicates otherwise.

As used herein, ranges can be expressed as from "about" one particular value, and/or to "about" another particular value. When such a range is expressed, an embodiment includes from the one particular value and/or to the other particular value. Similarly, when values are expressed as approximations, by the use of "about," it will be understood that the particular value forms another embodiment. It will be understood that the endpoints of each of the ranges are significant both in relation to the other endpoint and independently of the other endpoint. It will also be understood that there are a number of values disclosed herein, and that each value is also disclosed herein as "about" that particular value in addition to the value itself. For example, if the value "50" is disclosed, then "about 50" is also disclosed.

As used herein, the term "biological sample" refers to biological samples known in the art including, but not limited to, tissues, cells, proteins, and lipids. Biological samples may be native modified, or engineered, and include non-mammalian and mammalian samples, including human samples.

As used herein, the terms "patient" or "subject" include any mammal, including humans.

As used herein, the term "pharmaceutical" refers to articles intended for use in the diagnosis, cure, treatment, mitigation, or prevention of disease or biological disorders.

Referring to FIG. 1, there biomimetic array device 10 is depicted with its inlet region 12 for fluid application and cassette 14 for sample evaluation. Biomimetic array device 10 is of unitary construction in the instances depicted, though components or features are potentially manufactured separately and attached in embodiments not shown. The material used for the manufacture of biomimetic array device 10 is hydrophilic, and includes materials such as polylactic acid, acrylonitrile butadiene styrene, polyethylene terephthalate, polycarbonate, and nylon, though other materials are contemplated for use. In some instances, the material is polypropylene. To manufacture the biomimetic array device 10 depicted in FIG. 2, additive manufacturing techniques or injection molding are used. However, various manufacturing techniques and combinations of manufacturing techniques known in the art are suitable for the manufacture of biomimetic array device 10. Similarly, materials used in the manufacture of biomimetic array device 10 vary based on the choice of manufacturing technique. Generally, a 3D model of the intended biomimetic array device 10 is first produced and used to direct the accurate manufacture of biomimetic array device 10, including the desired dimensions and features. Biomimetic array device 10 is, in some instances, coated in regions with a hydrophobic material. The regions of coating include upper edges of cassette 14 of biomimetic array device 10, so that fluids within cassette 14 are not inadvertently spilled or otherwise inadvertently wet tops of adjacent walls under normal operation or agitation of biomimetic array device 10.

The dimensions of biomimetic array device 10 vary based on the number of fluids to be introduced in inlet region 12 and the number of microchamber arrays 20 included in cassette 14. The depth of cassette 14 is variable based on application, and allows fluid in microchambers 18 to interact with any biological sample 22 positioned on cassette 14. In some instances, the depth of cassette 14 ranges from millimeters to several centimeters. The depth of inlet region 12 is about the same as the depth of cassette 14 in some instances and is shallower or deeper in other instances. The thickness of cassette 14 is such that each microchamber 18 is accommodated with adequately thick walls separating adjacent microchannels 16 and microchambers 18 such that the size of biological sample 22 is minimized. For instance, cassette 14 with microchambers 18 that are about 300 μm thick and walls between microchambers 18 that are about 300 μm thick would accommodate these dimensions in the thickness of cassette 14. The width of inlet region 12 is greater than the width of cassette 14 in some instances and is less than or about equal to the width of cassette 14 in other instances. The length of cassette 14 is such that a desired number of microchamber arrays 20 are accommodated, along with microchannels 16 for fluid transport. In some instances, the length of cassette 14 ranges from several centimeters to several decimeters, though other lengths are possible. The length of inlet region 12 is less than the length of cassette 14 in some instances and is greater than or about equal to the length of cassette 14 in other instances.

Figure 2:
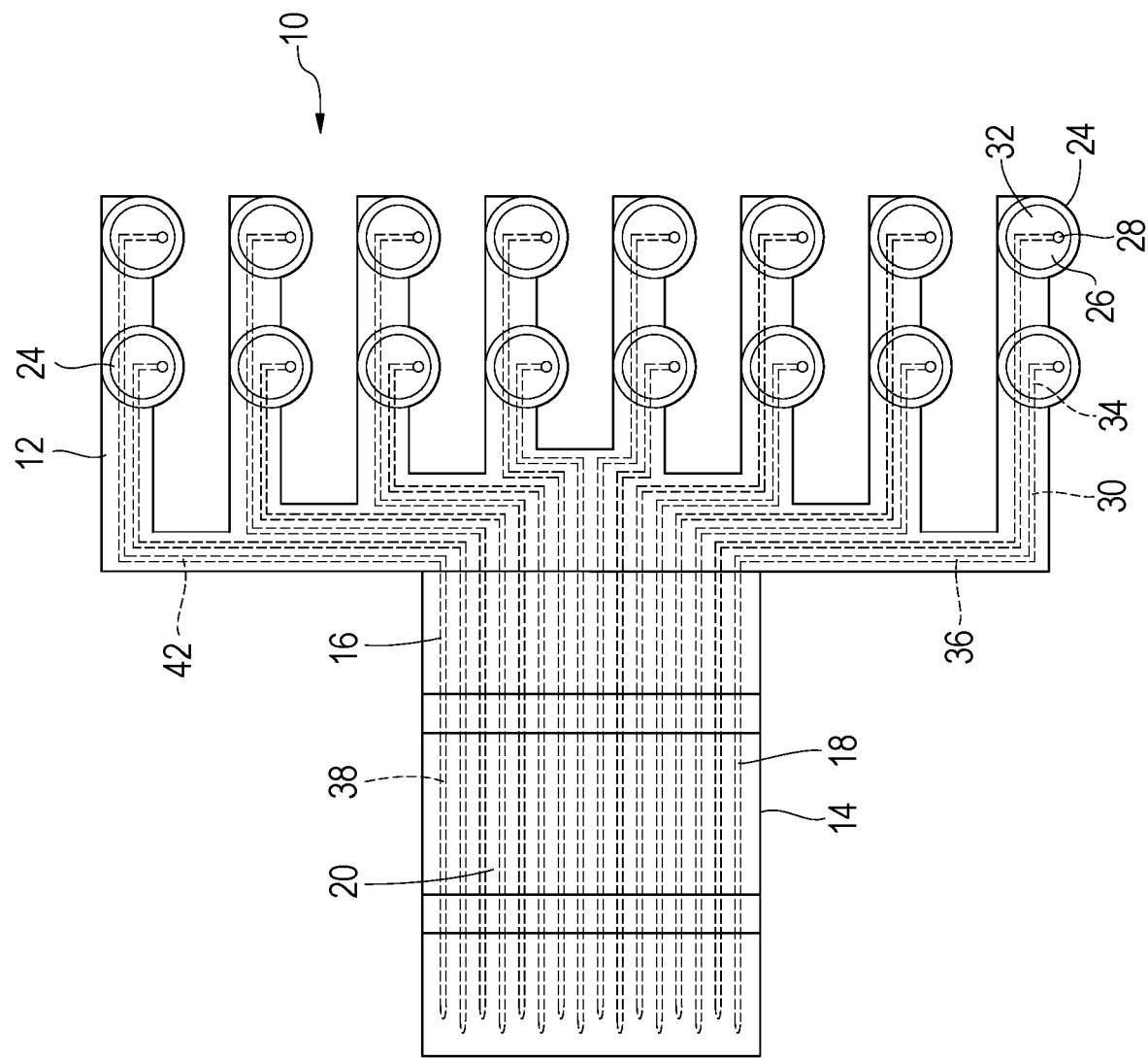
FIG. 2 is a top elevational view of the biomimetic array device of FIG. 1 showing wells with ports for conveying fluid into inlet channels in the inlet region of biomimetic array device.

As shown in FIG. 2, inlet region 12 of biomimetic array device 10 includes at least one well 24 to collect deposited fluid and direct the fluid to other regions within biomimetic array device 10. When a plurality of wells 24 are included, biomimetic array device 10 is configured to administer various fluids to biological sample 22. In other instances where a plurality of wells 24 are included, biomimetic array device 10 is configured to administer at least one fluid to biological sample 22 in at least duplicate, allowing for statistical analysis of sample-fluid interactions. Wells 24 are built into biomimetic array device 10 and are positioned in columns, rows, or other configurations. In some embodiments, wells 24 are spaced in each row such that commercial multi-channel pipettors are capable of dispensing fluid into each well 24 in one row at once. The number and shape of wells 24 is variable, though approximately equally-shaped wells 24 are used when biomimetic array device 10 is configured for use with a commercial multi-channel pipettors. The number of wells 24 in any row, in instances where a commercial multi-channel pipettors is used, also depends on the number of channels of the commercial multi-channel pipettors. For instance, eight wells 24 are in one row, as depicted in FIG. 2, though other numbers of wells 24 or rows of wells 24 are contemplated. Further, rows and/or columns have varying numbers of wells within one biomimetic array device 10 in some embodiments. The shape of wells 24 is shown to be approximately a circle as depicted in FIGS. 1 and 2, though other shapes, such as an oval, quadrilateral, or rounded quadrilateral are contemplated. Further, while the height and circumference of wells 24 in FIG. 2 are approximately equal, wells 24 within one inlet region 12 have varying dimensions in other embodiments not shown.

Referring to FIG. 2, each well 24 has a base 26 with a port 28 that spans base 26 to allow well 24 to be in fluid communication with an inlet channel 30. As shown in FIG. 2, each base 26 has the same cross sectional area as a top opening 32 of each well, though in embodiments not depicted the cross sectional areas of each base 26 and each top opening 32 differs. Fluid is administered to wells 24 though top openings 32 of wells 24 and collects within the interior of wells 24 defined by well sidewalls and base 26. Due to the hydrophilic material used in manufacturing each well 24 and gravitational forces, fluid flows toward base 26 after it is administered into well 24. Port 28 is depicted as circular in cross section in FIG. 2, though other shapes, such as a quadrilateral, an oval, or a rounded quadrilateral, are possible. Port 28 has a largest dimension ranging from several micrometers to several millimeters. Fluid within well 24 enters port 28 without the aid of external pressure sources, such as a pump, due to hydrophilic material properties, capillary forces, gravitational forces, and biomimetic array device 10 geometry.

Figure 3:
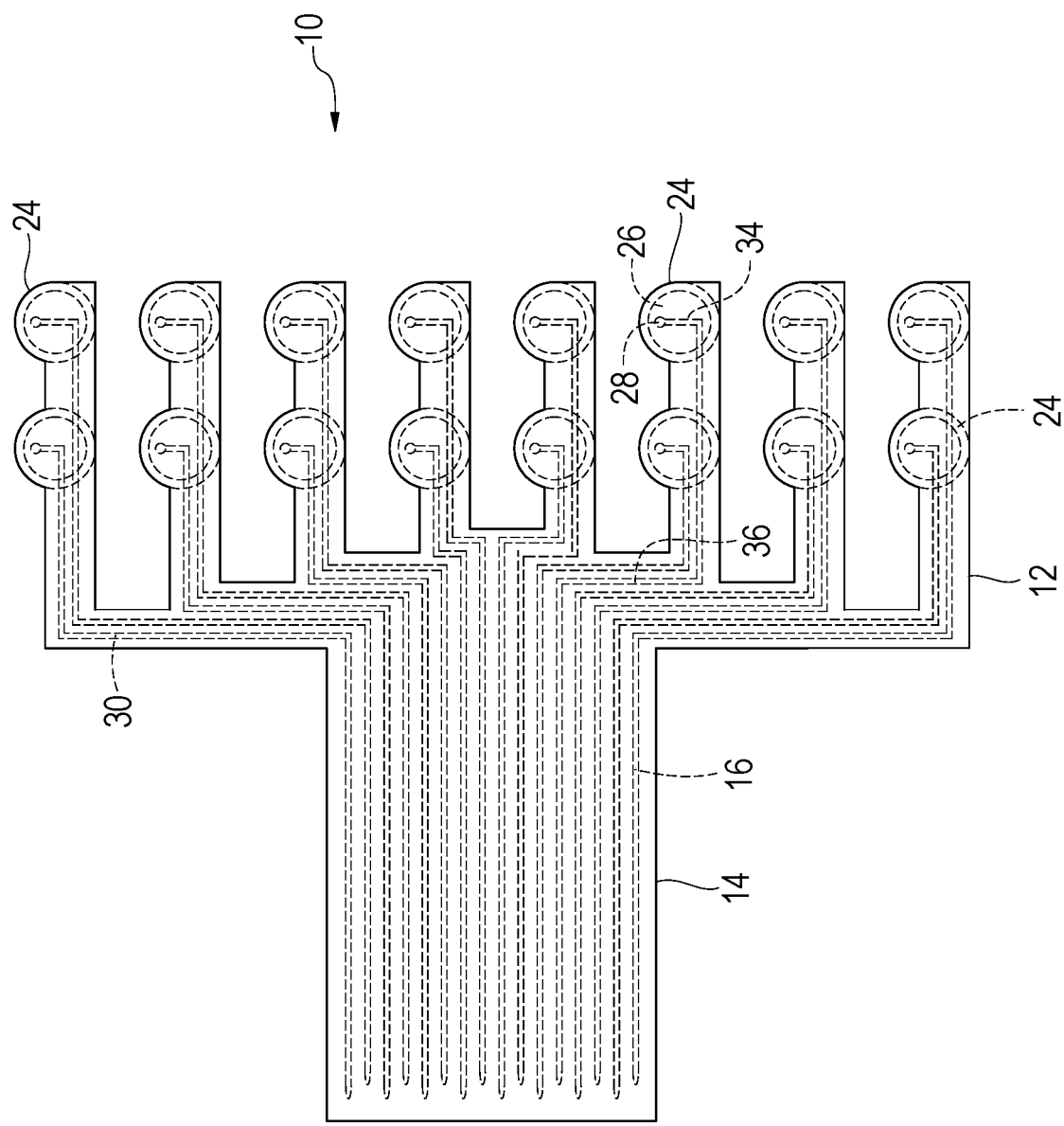
FIG. 3 is a bottom elevational view of the biomimetic array device of FIG. 1 showing fluid paths through wells, inlet channels, microchannels, and microchambers.

Referring now to FIG. 3, the fluid paths within inlet region 12 and cassette 14 are shown from a bottom view. In inlet region 12, each well 24 is in fluid communication with an intake region 34 of one inlet channel 30. Similarly, each intake region 34 of one inlet channel 30 is in fluid communication with one well 24. Thus, fluid that enters top opening 32 of well 24 is transported to intake region 34 of inlet channel 30 through port 28. Inlet channel 30 conveys fluid within inlet region 12 of biomimetic array device 10 and no portion of inlet channel 30 is open to the external environment in the embodiment depicted. However, in embodiments not depicted, inlet channel 30 is potentially open to the external environment in at least one portion of inlet channel 30. The cross section of inlet channel 30 is substantially equal to the cross section of port 28 in the embodiments depicted, though in other embodiments the cross section of inlet channel 30 differs from that of port 28. The cross sectional dimensions of inlet channel 30 remain substantially consistent throughout the length of inlet channel 30 in the embodiments depicted, though in other embodiments not shown the cross sectional dimensions of inlet channel 30 increase, decrease, or otherwise vary along the length of inlet channel 30. Additionally, cross sectional dimensions of all inlet channels 30 are the same in some instances, such as that depicted, or vary with individual inlet channels 30 in other instances. After fluid enters inlet channel 30 in intake region 34, it flows through a transport region 36 of inlet channel 30. In some embodiments that are not shown, inlet channels 30 form branches within their transport region 36, such that fluid from one well 24 is divided evenly to each branch. In the embodiment shown in FIGS. 2-3, inlet region 12 is wider than cassette 14, and inlet channels 30 transport fluid from each well 24 to a region where inlet channels 30 meet microchannels 16. Thus, some inlet channels 30 are longer than other inlet channels 30 based on the geometry of biomimetic array device 10. Adjustments to biomimetic array device 10 that allow the transport of equal volumes of fluid and equal exposure of biological sample 22 to the fluid are discussed below.

Fluid enters microchannels 16 of cassette 14 from transport region 36 of inlet channels 30. In instances where inlet channels 30 branch, each branch meets one microchannel 16. In unbranched inlet regions, each inlet channel 30 transports fluid to one microchannel 16 and each microchannel 16 is in fluid communication with one inlet channel 30.

Figure 4:
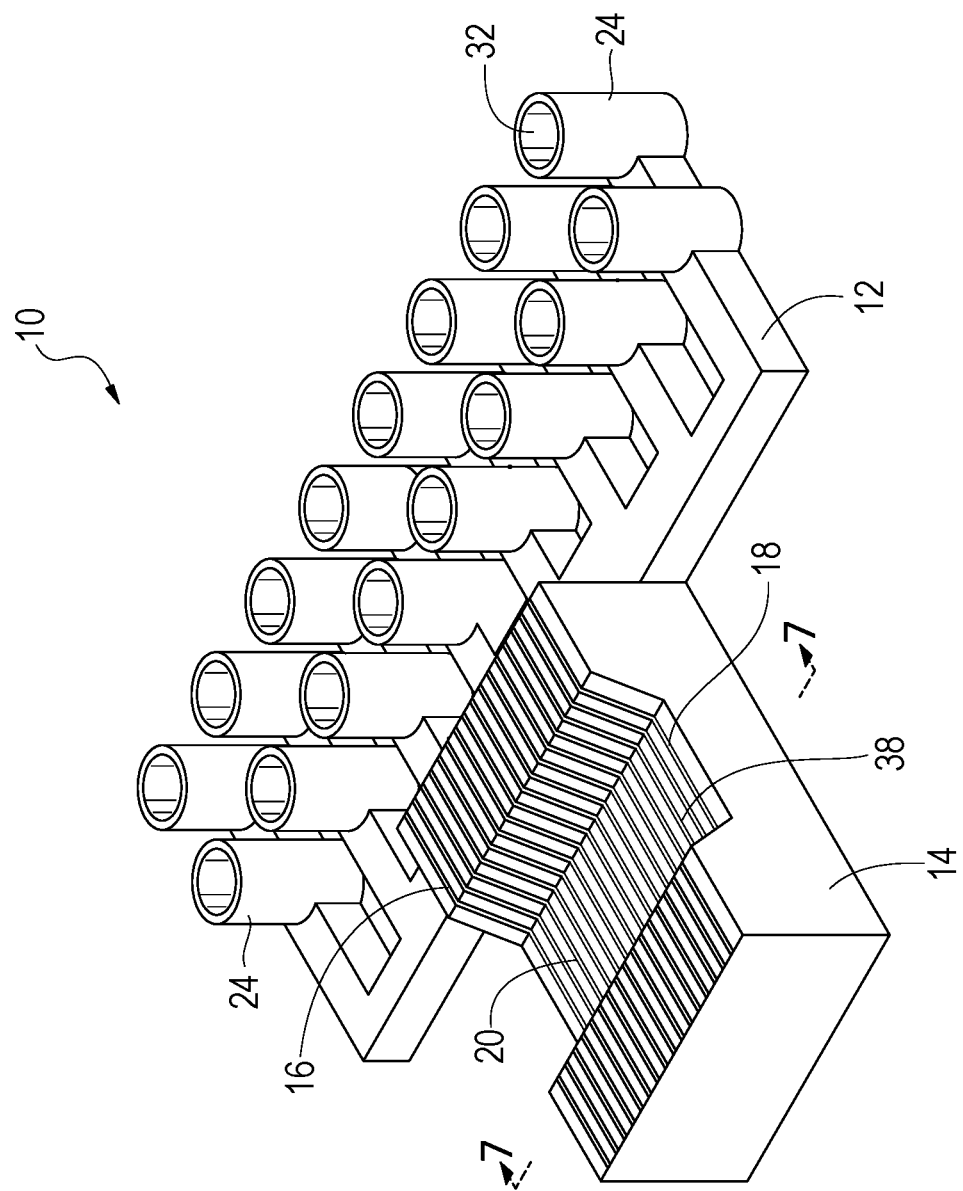
FIG. 4 is a side perspective view of the biomimetic array device of FIG. 1 showing the shape of the cassette, with lower sidewalls along microchambers and longer sidewalls along microchannels.

Referring to FIG. 4, cassette 14 has microchannels 16 that are configured to transport fluid to microchambers 18 within a microchamber array 20. While one microchamber array 20 is depicted in FIG. 4, two or more microchamber arrays 20 are possible and are connected either in parallel, in series, or in both parallel and series. When cassette 14 is viewed from a side as in FIG. 4, microchamber arrays 20 are shown to have shorter sidewalls than areas that comprise only microchannels 16. Thus, cassette 14 has a U-shaped or stepped shape in profile, where the valley of each U-shape or lower step indicates the location of one microchamber array 20. This lower sidewall region allows for biological sample 22 to be placed at a top interface 38 of microchambers 18 within one microchamber array 20. Additionally, the U-shape or stepped shape reduces or substantially prevents fluid from spilling from cassette 14 during normal operation or during agitation of biomimetic array device 10.

Microchannels 16 branch before reaching a microchamber 18 in instances not depicted, or do not branch as shown in FIGS. 1-2. Microchannels 16 are substantially linear in instances where there is one microchamber array 20 as depicted or where microchamber arrays 20 are arranged in series. In other instances, such as when microchamber arrays 20 are arranged in parallel, microchannels 16 are not linear. As shown in FIG. 4, microchannels 16 are in fluid communication with microchambers 18, and one microchannel 16 is in fluid communication with one microchamber 18. Microchannels 16 extend from a downstream end of microchambers 18 in embodiments such as those depicted, though microchannels 16 terminate after a final microchamber array 20 in embodiments not shown. The combined length of microchambers 18 and microchannels 16 is equal in some instances or varies in other instances, which are discussed below. Within cassette 14, microchannels 16 and microchambers 18 have substantially equal widths, which may be, for example, 300 μm. The cross sections of microchannels 16 and microchambers 18 differs from that of inlet channels 30 in the instance depicted in FIG. 4, though these cross sections are substantially equal in other instances. Cross sections of microchannels 16 and microchambers 18 are, for example, that of a U-shape or a quadrilateral with its top side removed. The depth of microchannels 16 and microchambers 18 is discussed below in greater detail, though all depths are equal in some instances and vary in others. Microchannels 16 and microchambers 18 are open to the external environment at their top interface 38, which is opposite their base. Sidewalls dividing adjacent microchannels 16 and microchambers 18 have the same thickness as each microchannel 16 or microchamber 16 in FIG. 3, though sidewall thicknesses are potentially greater than or less than the thicknesses of microchannels 16 and microchambers 18. Microchannels 16 and microchambers 18 are equally spaced within cassette 14 in the embodiments depicted, though spacing may vary in other embodiments.

Referring back to FIG. 4, microchambers 18 include top interface 38 that provides a region for the interaction of fluid with any biological sample 22 placed at top interface 38. Top interface 38 is depicted as being open to the external environment, though in embodiments not depicted top interface 38 includes a permeable or semi-permeable interface between microchambers 18 and biological sample 22. In some instances, biological sample 22 exposure to and interaction with fluids occurs immediately when fluid fills microchamber 18 and in other cases top interface 38 provides a delayed release of fluids or components of fluids from microchamber 18 to biological sample 22.

In some embodiments, microchannels 16, inlet channels 30, and/or microchambers 18 include agitation structures 42 to aid in the mixing of fluid components as then travel through microchannels 16, inlet channels 30, and/or microchambers 18. Agitation structures 42 are semi-circular, rod-shaped, branched rods, spherical, or any other structure that extends from an interior surface of microchannels 16, inlet channels 30, and/or microchambers 18 and mixes fluid as fluid moves past it. Agitation structures 42 are attached or built into the interior walls and/or base of microchannels 16, inlet channels 30, and/or microchambers 18 and extend from these interior surfaces into the fluid path within microchannels 16, inlet channels 30, and/or microchambers 18, such that movement of fluid past agitation structures 42 induces at least some degree of turbulent flow, mixing the fluid. In some instances, agitation structures 42 are aided in their mixing function by movement or agitation of biomimetic array device 10. For example, biomimetic agitation device 10 is placed on a commercial rocker, shaker or other vibrational or agitation equipment to provide agitation or motion.

Figure 5:
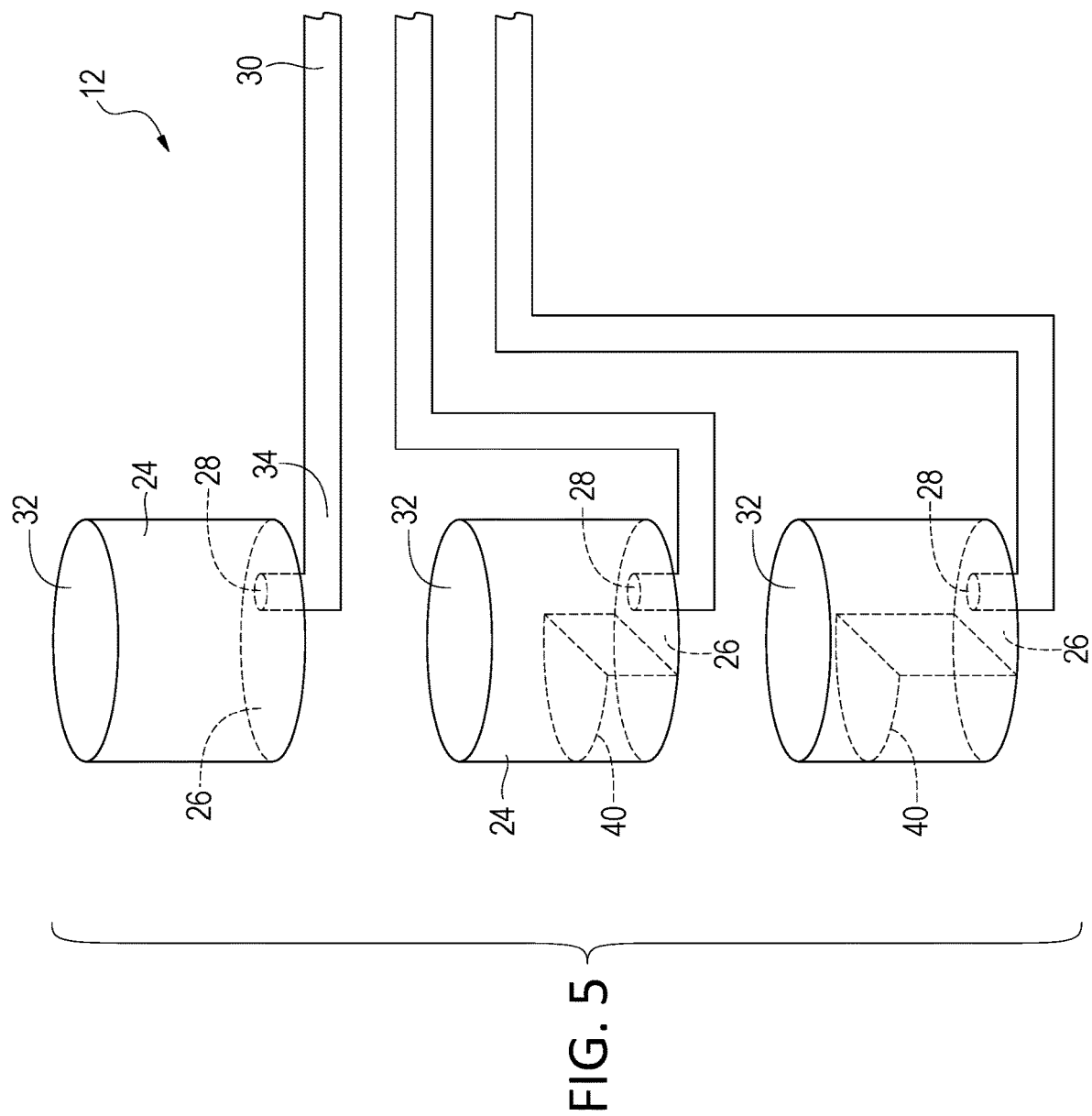
FIG. 5 is a perspective enhanced view of the wells of the biomimetic array device of FIG. 1 showing embodiments where spacing structures alter fluid height within wells.

Referring to FIG. 5, some embodiments include wells 24 with spacing structures 40. Spacing structures 40 are included within wells 24 to alter the height of fluid from base 26. Thus, equal volumes of fluid deposited in multiple wells 24 containing spacing structures 40 of various sizes results in various fluid heights. As such, in some embodiments biomimetic array device 10 is configured such that wells 24 in fluid communication with longer inlet channels 30 have larger spacing structures 40 than wells 24 in fluid communication with shorter inlet channels 30. In sizing spacing structures 40 according to inlet channel 30 length, equal volumes of fluid applied to wells 24 result in equal volumes of fluid reaching biological sample 22 and equal exposure of fluid from microchambers 18 to biological sample 22. Spacing structures 40 are positioned such that port 28 is not blocked or impeded and such that deposited fluid reaches and is transported through port 28. The cross sectional shape of spacing structure 40 parallel to base 26 is a circle, semi-circle, quadrilateral, oval, rounded quadrilateral, or any other cross sectional shape that fits within well 24 without blocking or impeding fluid access to port 28. Spacing structure 40 is shown in FIG. 5 to conform to at least some regions of the sidewall of well 24, though in embodiments not shown spacing structure 24 does not conform to any sidewall of well 24. Extending from base 26, spacing structure 40 reaches a height within well 24 that is less than or equal to the height of the sidewall of well 24. Sizes of spacing structures 40 are varied by altering dimensions of spacing structures 40, such as the height and cross sectional area parallel to base 26. In some cases, some wells 24 have spacing structures 40 while other wells do not. In other cases, all wells 24 or no wells 24 have spacing structures 40. In some embodiments, the presence, absence, and size of spacing structures 40 within wells 24 is determined by biomimetic array device 10 geometry, so that wells 24 nearest cassette 14 with shorter inlet channels 30 that reach cassette 14 have no spacing structure 40 the smallest spacing structures 40. Similarly, wells 24 farthest from cassette 14 with longer inlet channels 30 that reach cassette 14 have the largest spacing structures. In embodiments where wells 24 position relative to cassette 14 does not correlate with inlet channel 30 length, inlet channel length 30 determines the size and presence or absence of spacing structures 40, with wells 24 in fluid communication with longer inlet channels 30 having larger spacing structures 40. Larger spacing structures 40 encompass larger volumes of the interior of wells 24 than smaller spacing structures 40, so that equal volumes of fluid applied to wells 24 will have a greater height from base 26 in wells with larger spacing structures 40 than in wells with no or smaller spacing structures 40. In some embodiments not depicted, more than one spacing structure 40 is present in at least one well 24, allowing that port 28 is not blocked or impeded from fluid transport. Spacing structures 40 are sized and shaped such that they do not impede a pipette or other fluid depositing means from providing fluid to well 24. As depicted in an embodiment in FIG. 5, spacing structures 40 are built into well 24 and are of unitary construction with well 24, while in other embodiments that are not depicted, spacing structures are formed separately from well 24 and attached by attachment means known in the art. In these embodiments, spacing structures 40 are made from the same material that well 24 is composed of, or are made from a different material. Spacing structures 40 are hollow, partially hollow, or solid, but are substantially impermeable to fluid. While the use of spacing structures 40 allows equal volumes to be dispensed and transported to biological sample 22 with approximately equal exposure of biological sample 22 to each fluid, some embodiments without spacing structures 40 instead use the dispensation of unequal volumes of fluid to wells 24 based on inlet channel 30 distance to cassette 14 to achieve this same result. These unequal volumes are calculated prior to dispensation, though the use of spacing structures 40 simplifies this process for a user by eliminating these calculations.

Figure 6:
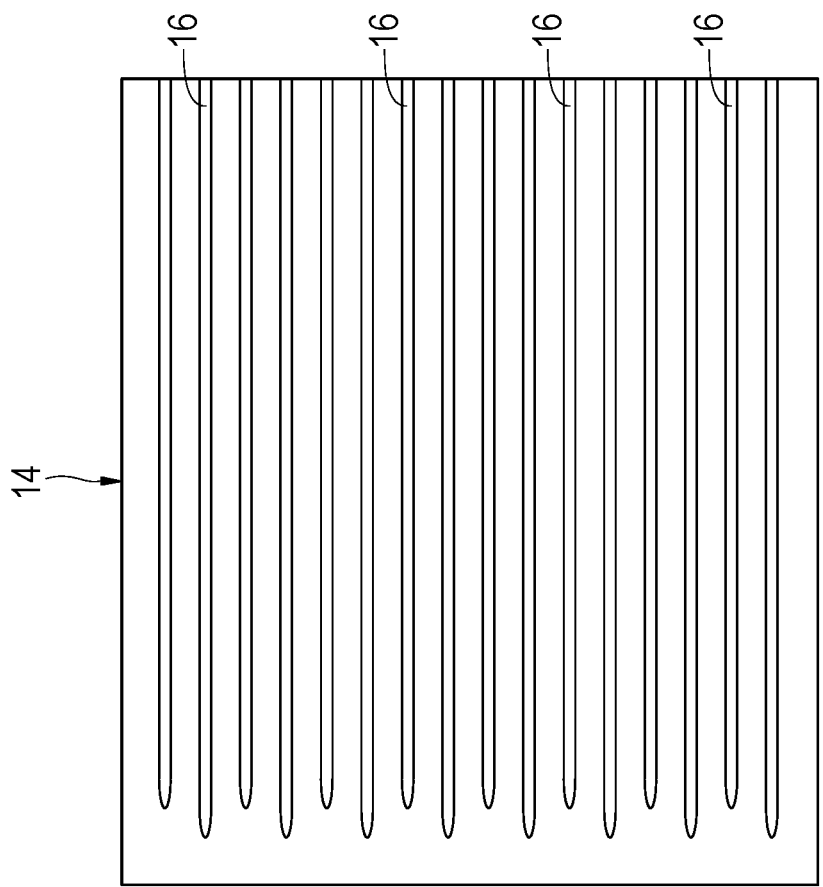
FIG. 6 is a top view of the terminus of microchannels and microchambers of an embodiment of the biomimetic array device of FIG. 1, where no adjacent microchannels or microchambers terminate at the same length.

Referring now to FIG. 6, in some embodiments, microchannels 16 and microchambers 18 are produced so that they terminate at various points across the length of cassette 14. FIG. 6 depicts microchannels 16 that alternate between longer and shorter microchannels 16. However, in other embodiments not depicted microchambers 18 alternate between longer and shorter microchambers 18 as well. The varying lengths are produced to prevent leakage from micron-scale holes that may form at the intersection of bases and sidewalls of microchannels 16 and microchambers 18 during manufacture. By ensuring that no adjacent microchannels 16 or microchambers 18 share a common terminal sidewall, leaks between adjacent microchannels 16 or microchambers 18 are substantially prevented. FIG. 6 depicts two alternating microchannel lengths, though more than two lengths of microchannels 16 or microchambers 18 are present in other embodiments not shown.

Figure 7:
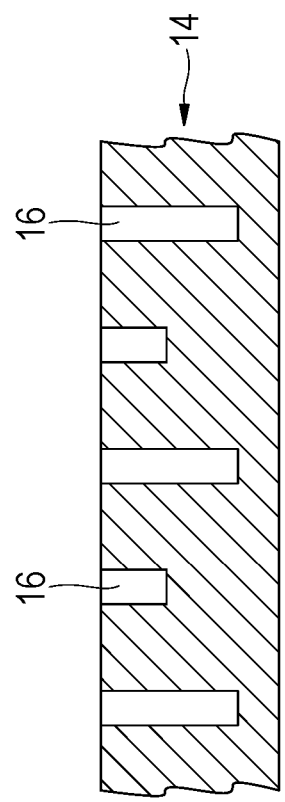
FIG. 7 is a sectional view of microchannels and microchambers within the cassette of the biomimetic array device of FIG. 1, which, in certain embodiments, has no adjacent microchannels or microchambers extending to the same depth within the cassette.

In FIG. 7, a cross section of cassette 14 is shown with microchannels 16 of varying depths within cassette 14. In cross sections similar to that of FIG. 7 that are not shown, microchambers 18 also have varying depths within cassette 14. Similar to that described above, micron-scale holes may form at the intersection of bases and sidewalls of microchannels 16 and microchambers 18 during manufacture. Thus, in some embodiments, no adjacent microchannels 16 or microchambers 18 have the same depth to substantially prevent leakage between microchannels 16 and microchambers 18 from any micron-sized holes. While two depths of microchannels 16 and microchambers 18 are depicted, more than two depths of microchannels 16 and microchambers 18 are possible in embodiments not shown.

In some embodiments where microchannel and microchamber lengths are varied, microchannel and microchamber depths are also varied with microchannel and microchamber widths remaining equal. In these embodiments, equal fluid volume capacity is maintained in each microchannel 16 and microchamber 18 by having longer microchannels 16 and microchambers 18 be relatively shallower and by having shorter microchannels 16 and microchambers 18 be relatively deeper. Thus, equal volumes of fluid reach microchambers 18 and any biological sample 22 at top interface 38 of microchambers 18. In other embodiments where microchannel or microchamber length and depths are varied, fluid volume capacity within each microchannel 16 or microchamber 18 is not equal.

Figure 8:
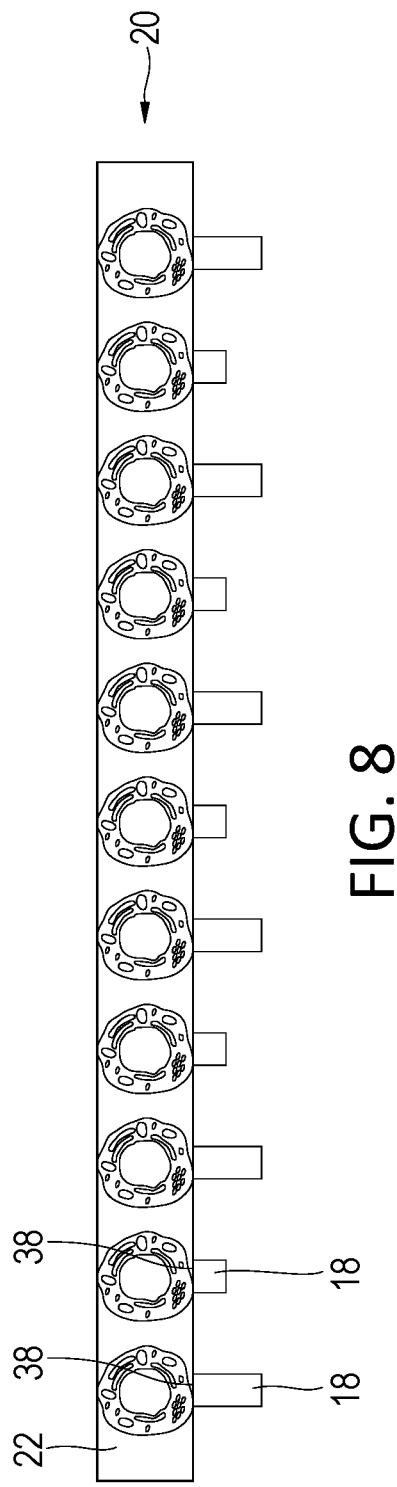
FIG. 8 is a sectional view of microchambers and a biological sample placed on the biomimetic array device of FIG. 1, where fluids interact with the biological sample at the top interface of each microchamber.
Figure 9:
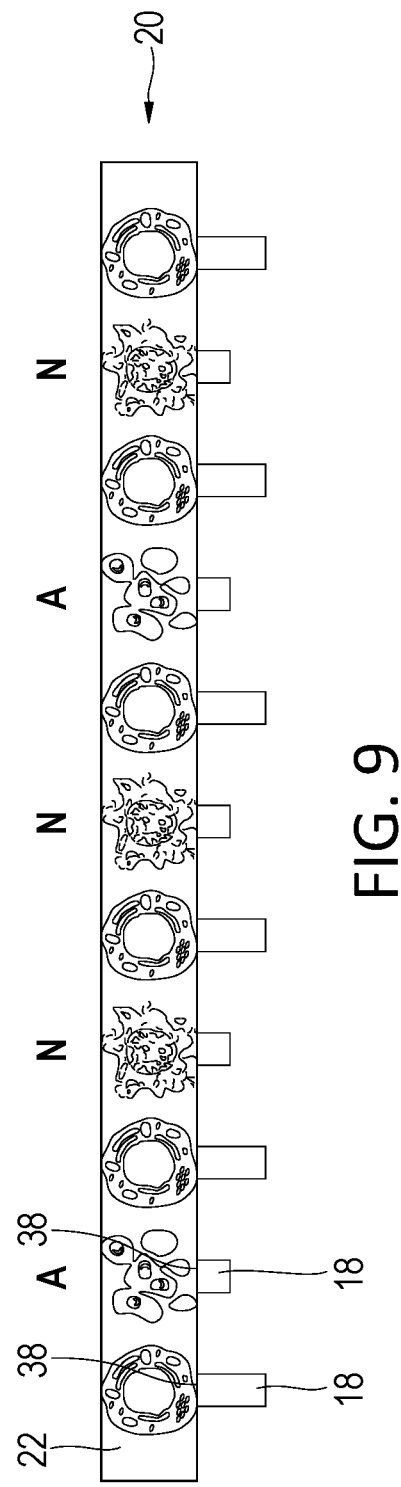
FIG. 9 is a sectional view of microchambers and a biological sample placed on the biomimetic array device of FIG. 1, where different fluids interacting with the biological sample result in different cell response and viabilities within the biological sample.

FIGS. 8 and 9 depict a cross section of a top region of cassette 14, where fluids interact with biological sample 22 at top interface 38 of each microchamber 18. Different fluids are depicted and cells within biological sample 22 are exposed to these fluids in FIG. 8. Examples of fluids include culture media, wash solutions, labeling solutions, pharmaceutical compounds, therapeutic agents, analytes, or other solutions for interaction with biological samples 22. When an array of therapeutic agents is utilized, multiplexed testing of the efficiency of therapy regimens is possible using a patient's biological sample 22, allowing fast and low cost identification of promising therapies. When an array of pharmaceutical agents is utilized, it is possible to test the effectiveness of several candidate compounds or molecules simultaneously, aiding in selection of the most effective compounds. When particular fluids are applied in duplicate or greater, statistical analysis of results is possible. Similarly, when a portion of fluids in an array are healthy culture media and another portion of fluids in the array are analytes, such as therapeutic agents or pharmaceutical compounds, the healthy culture media serves as a control for normal cell morphology, phenotype, and viability from which comparisons with analytes are made.

In FIG. 9, fluids from microchambers 18 have been incubated on regions of biological sample 22 and these regions can be analyzed with respect to cell viability, phenotype, response, and morphology to determine the effects of the fluids. For instance, healthy media incubation results in a standard, expected cell morphology and proliferation profile, with cell counts that may serve as a baseline or control for other analytes. Thus, analytes that result in lower cell counts or abnormal cell morphologies, apoptotic indices or necrotic indices, or staining patterns are identified relative to controls. Cell morphologies for dead or unhealthy cells are bloated or exploded for necrotic cell death or have blebbing for apoptotic cell death. When the analyte is taken up by the region of biological sample 22 at top interface 38 of microchamber 18 that provides the analyte and apoptosis is observed, cells are determined to have been induced by analyte to program or initiate their own death. Necrosis indicates, in some instances, that cells did not take up the analyte or that cells lacked essential nutrients or growth conditions. Staining techniques, such as those using fluorescent molecules, are used to indicate live or dead cells in some instances. For example, propidium iodide and/or Annexin V provide visible information regarding cell viability.

In order to observe regions of biological sample 22 and the cells within biological sample 22, imaging techniques are used. Generally, microscopy is used to observe biological sample 22 at a cellular level, with confocal microscopy providing images of biological tissue 22 in one or more z-planes. Thus, confocal microscopy allows analysis of cells within biological sample 22 not only on the surfaces of biological sample 22, but within biological sample 22. Fluorescence channels are viewed using a microscope to observe staining patterns, where different channels are available to view different fluorophores.

In some instances, fluid from each microchamber 18 in microchamber array 20 is analyzed after fluid has been in contact with biological sample 22. Fluid analysis is conducted using methods such as enzyme-linked immunosorbent assay (ELISA), enzyme-linked immunospot (ELISPOT), and Western blotting, to identify and/or quantify fluid components, such as antibodies or proteins, which may vary based on fluid identity and biological sample exposure. In other instances, DNA or RNA is detected in fluid in microchambers 18 after the fluid has been in contact with biological sample 22. Techniques such as gel electrophoresis, Northern blotting, Southern blotting, or polymerase chain reaction and sequencing may be used to detect and identify nucleic acids. Other techniques and methods not specifically described above for the detection, identification, and/or quantification of nucleic acids, proteins, antibodies, or other cellular components are contemplated for the present disclosure.

Biological sample 22 is includes any tissue, cell, protein, lipid, or other biological material. Biological samples 22 are, in some instances, freshly provided from a patient or subject or frozen samples that were originally provided by a patient or subject. Biological samples 22 further are natural, modified, or at least partially engineered materials. In some cases, biological sample 22 includes or is composed of unexpanded cells, while in other cases some or all cells of biological sample 22 are expanded. Sample washing and preservation techniques are used in the preparation and storage of biological sample 22 in some cases, while in other cases biological sample 22 is not exposed to preservation materials, growth factors, or other added solution components. In some embodiments, biological sample 22 is a tissue slice culture from a tumor biopsy of a patient. Fresh or flash-frozen tumor biopsy specimens are compatible with the present invention. In other embodiments, biological sample 22 includes biological components that are adsorbed, bonded, or grown on a scaffold, including an elastomer spun scaffold, according to methods known in the art. Biological sample 22 is typically less than about 500 μm in thickness, though thicknesses ranging from about 100 μm to about 1 mm are contemplated as compatible with the present disclosure. Biological sample 22 is laid transversely across one microchamber array 20 so that each microchamber 18 within microchamber array 20 is positioned beneath biological sample 22. The positioning of biological sample 22 allows fluid to be wicked, and often the top surface of biological sample 22 that faces away from top interface 38 is less saturated than the surface of biological sample 22 that is in contact with top interface 38, forming a concentration gradient so that wicking of fluid from microchannels is possible.

In one example, biological sample 22 is a fresh tumor tissue sample collected by core needle biopsy using a 14-gauge needle. A tissue slice culture that is about 300 μm thick is prepared from the core specimen and placed on a porous polymer membrane culture insert. Biological sample 22 is then acclimated with pre-warmed medium and transferred onto a sterilized biomimetic array device 10 at top interfaces 38 of microchambers 28 within one microchamber array 20. Sterilization of biomimetic array device 10 is undertaken using methods known in the art, including, but not limited to UV radiation and application of an ethanol solution. The position of biological sample 22 is such that the basal surface of biological sample 22 is in direct or approximately direct conformal contact with top interface 38 of microchambers 18, while the apical surface is facing upwards to the external environment. Fluid is provided through microchannels 16 to microchambers 18 and biomimetic array device 10 is placed in a tissue culture incubator at approximately 37° C. with 5% $CO_2$. Incubation occurs over time periods ranging from several minutes to several days, or, as in this example, from 3 to 14 days. Alternatively, in some instances fluid is instead applied and incubated in different temperature and culture conditions. Returning to the example, cell viability and morphology within areas of biological sample 22 is investigated. Viability and proliferation are examined using staining techniques, such as staining biological sample 22 with propidium iodide and Annexin V, flowed by imaging of cells within biological sample 22 using a microscope, such as a confocal microscope. Several z-planes within biological sample 22 are assessed so that viability and proliferation can be assessed, such as through visualizing staining patterns, determining cell numbers through cell counts, or observing cell morphology. In another example, the above procedure is followed using a tissue slice culture prepared from a larger, bulk specimen instead of a core needle biopsy.

In yet another example, the tumor biopsy is first flash frozen prior to analysis. In this case, either core needle biopsy or larger specimen samples are placed in sterile cryotubes or other sterile containers fit for frozen storage. The storage containers also include 95% tissue culture medium or fetal bovine serum with 5% dimethyl sulfoxide. Each sample is treated according to established bio-banking protocols and samples storage containers are placed in secondary freezing containers with isopropanol and then transferred to a −80° C. freezer for approximately 24 hours. Following this, samples are transferred to liquid nitrogen storage for a duration that ranges from several days to years, or more specific to this example, about one to four weeks. After this storage duration, samples are thawed according to established bio-banking protocols. After thawing and washing of samples to remove storage agents, samples are prepared as fresh biological samples 22 as described above.

In some embodiments, following analysis of biological sample 22 and regions that were in contact with various analytes and fluids, information is obtained regarding the effectiveness of each fluid. When fluids are potential therapeutic agents, those therapeutic agents that effectively lead to tumor cell death are identified as candidates for administration to the patient from which the tumor biopsy was provided. Thus, instead of the time consuming, expensive, and inefficient typical method of administering a therapeutic regimen to the patient, evaluating effectiveness, and switching to a different therapeutic regimen if the original regimen is not successful, the present disclosure provides a method by which multiple therapeutic agents are tested for effectiveness in killing tumor cells in a patient's tumor in a low cost, fast, and efficient manner. The patient is able to avoid unnecessary and ineffective therapies and initiate those therapeutic regimens most likely to be effective, generally initiating effective therapies earlier than would occur using the conventional iterative approach.

Biomimetic array device 10 is configured to transport fluids without the aid of external mechanical force provided by, for instance, a pump. Device geometry, capillary forces, gravitational force, and material properties instead provide the ability for fluid to flow within biomimetic array device 10. However, in embodiments not shown, external mechanical devices are used in addition to device properties.

The present invention is capable of supporting various configurations of microchannels 16, microchambers 18, microchamber arrays 20, and wells 24, including a-k-d-n configurations where (a) is any number of microchamber arrays 20, (k) is any number of wells 24, (d) is any number of microchambers 18 connected to each well 24 by (n) number of microchannels 16. These components of the a-k-d-n configurations are capable of being connected in parallel, series, or any combination thereof. For instance, a 1-1-1-1 configuration includes one microchamber array 20 with one well 24 connected to one microchamber 18 by a single microchannel 16. In an exemplary 3-16-1-1 waterfall configuration, three microchamber arrays 20 are provided fluid by 16 wells 24, each well 24 connected to one microchamber 18 within each microchamber array 20 by one microchannel 16. Thus, in this exemplary waterfall configuration, there are 16 microchambers 18 within each microchamber array 20. When microchamber arrays 20 are in a series format, one microchannel 16 connects one microchamber 18 within one microchamber array 20 to one microchannel 16 within another microchamber array 20.

As will be understood by those familiar with the art, the present invention may be embodied in other specific forms without departing from the spirit or essential characteristics thereof. The present disclosure may be applied to other fields with applications not specifically described herein, such as for drug discovery, chemical energy storage exploration, biofabrication, and diagnostic imaging. Accordingly, the disclosures and descriptions herein are intended to be illustrative, but not limiting, of the scope of the invention which is set forth in the following claims.

We claim:

1. A biomimetic array device comprising:
   a cassette with at least one microchamber array and at least one microchannel, each microchamber array comprising at least one microchamber in fluid communication with at least one microchannel, and
   at least one well in fluid communication with at least one inlet channel,
   wherein each microchamber has a top interface that is open to its external environment and configured to receive a biological sample along said top interface, such that the biological sample at the top interface is positioned to draw fluid from the at least one microchamber when the at least one microchamber contains fluid, and
   wherein the biomimetic array device is configured to transport approximately equal volumes of fluid from each well to each microchamber.

2. The device of claim 1, wherein each well is configured to receive fluid through a top opening and direct said fluid to the at least one inlet channel though a port located in a base of the at least one well, each inlet channel configured to receive fluid from one well and transport the fluid to the at least one microchannel in the cassette.

3. The device of claim 1, wherein the at least one microchannel includes a plurality of microchannels having varying depths within the cassette and no adjacent microchannels of the plurality of microchannels having the same depth.

4. The device of claim 1, wherein the at least one microchannel includes a plurality of microchannels having varying lengths across the cassette and no adjacent microchannels of the plurality of microchannels having the same length.

5. The device of claim 1, wherein sidewalls of the cassette are higher along the at least one microchannel and lower along the at least one microchamber.

6. The device of claim 1, wherein the at least one microchannel and/or the at least one inlet channel comprises agitation structures.

7. The device of claim 1, wherein the at least one well contains a spacing structure within its interior that reduces a cross sectional area parallel to its base.

8. A biomimetic array device comprising:
   a cassette with at least one microchamber array and at least one microchannel, each microchamber array comprising at least one microchamber in fluid communication with at least one microchannel, and
   at least one well in fluid communication with the at least one inlet channel,
   wherein each microchamber has a top interface that is open to its external environment and configured to receive a biological sample along said top interface, such that the biological sample at the top interface is positioned to draw fluid from the at least one microchamber when the at least one microchamber contains fluid,
   wherein the at least one well contains a spacing structure within its interior that reduces a cross sectional area parallel to its base, and
   wherein sizes of the spacing structures are determined by lengths of the inlet channels, with larger spacing structures in wells that are in fluid communication with longer inlet channels, such that the device is configured to transport equal volumes of fluid deposited into each well to each microchamber within the at least one microchamber array and to provide equal exposure of fluid to the biological sample at the top interface of each microchamber.

9. A method of using a biomimetic array device comprising the steps of:
   providing a cassette with at least one microchamber array, at least one microchannel, and at least one well, each microchamber array including at least one microchamber in fluid communication with the at least one microchannel and the at least one well,
   positioning a biological sample along a top interface of the at least one microchamber array, and
   depositing fluid within the at least one well,
   wherein the fluid flows through the at least one microchannel and the at least one microchamber, such that the at least one microchamber within the at least one microchamber array provides an approximately equal volume of fluid to the biological sample at the top interface of each microchamber in the at least one microchamber array.

10. The method of claim 9, wherein an equal volume of fluid is deposited in each well.

11. The method of claim 9, wherein the fluid deposited in any well of the at least one well is selected from the group consisting of culture media, a therapeutic agent, or a pharmaceutical compound.

12. The method of claim 9, wherein the biological sample comprises tumor tissue from a patient.

13. The method of claim 12, further comprising the step of characterizing the viability of cells within the tumor tissue after exposure to fluid, such that fluids that result in cell death are identified as therapeutic candidates for the patient.

14. A biomimetic array device comprising:
   a cassette including a plurality of microchannels and a plurality of microchambers with at least one microchamber of the plurality of microchambers being in fluid communication with at least one microchannel of the plurality of microchambers,
   wherein the plurality of microchannels have alternating depths and alternating lengths with longer microchannels being more shallow and shorter microchannels being deeper, such that the plurality of microchannels are configured to hold equal volumes of fluid and such that fluid transport between adjacent microchannels is substantially prevented.

15. The device of claim 14, wherein the at least one microchamber includes a top interface that is open to its external environment.

16. The device of claim 14, further comprising at least one well and at least one inlet channel, the at least one well being configured to receive fluid and direct said fluid into the at least one inlet channel though a port located in a base of the at least one well, the at least one inlet channel being configured to transport fluid to the at least one microchannel in the cassette.

17. The device of claim 16, wherein the at least one well contains a spacing structure within its interior that reduces a cross sectional area parallel to its base, such that the at least one well is configured to hold a volume of fluid at a greater height within its interior than would occur for the same volume of fluid without the spacing structure.

18. The device of claim 17, wherein sizes of the spacing structures are determined by lengths of the inlet channels, which fluidly couple the plurality of microchannels and the plurality of microchambers with larger spacing structures in wells that are in fluid communication with longer inlet channels, such that the device is configured to transport equal volumes of fluid deposited into each well to each microchamber within one microchamber array and to provide equal exposure of fluid to the biological sample positioned at the top interface of each microchamber.

* * * * *